United States Patent
Liu et al.

(10) Patent No.: US 8,771,317 B2
(45) Date of Patent: Jul. 8, 2014

(54) INTERSPINOUS PROCESS IMPLANT AND METHOD OF IMPLANTATION

(75) Inventors: Mingyan Liu, Bourg-la-Reine (FR); Jeffrey Zhang, Collierville, TN (US); Loic Josse, Denens (CH)

(73) Assignee: Warsaw Orthopedic, Inc., Warsaw, IN (US)

( * ) Notice: Subject to any disclaimer, the term of this patent is extended or adjusted under 35 U.S.C. 154(b) by 744 days.

(21) Appl. No.: 12/607,917

(22) Filed: Oct. 28, 2009

(65) Prior Publication Data

US 2011/0098745 A1  Apr. 28, 2011

(51) Int. Cl.
*A61B 17/70* (2006.01)

(52) U.S. Cl.
USPC ...................................... 606/249

(58) Field of Classification Search
USPC ............. 606/249, 246–248; 623/17.11, 17.15
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,426,364 A | 2/1969 | Lumb |
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,401,112 A | 8/1983 | Rezaian |
| 4,519,100 A | 5/1985 | Willis et al. |
| 4,553,273 A | 11/1985 | Wu |
| 4,554,914 A | 11/1985 | Kapp et al. |
| 4,573,454 A | 3/1986 | Hoffman |
| 4,599,086 A | 7/1986 | Doty |
| 4,604,995 A | 8/1986 | Stephens et al. |
| 4,611,582 A | 9/1986 | Duff |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

"Dispositivo Intervertebrale Ammortizzante DIAM," date unknown, p. 1.

(Continued)

*Primary Examiner* — Pedro Philogene
*Assistant Examiner* — David Comstock

(57) ABSTRACT

Medical devices for the treatment of spinal conditions are described herein. The medical device of this invention includes a spacer that is disposed between adjacent spinous processes and has a proximal retention member and a distal retention member, which may be rotated with respect to the proximal retention member between an initial implantation configuration and a final locked configuration.

16 Claims, 13 Drawing Sheets

(56) References Cited

U.S. PATENT DOCUMENTS

| | | |
|---|---|---|
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,458,641 A | 10/1995 | Ramirez Jimenez |
| 5,474,561 A * | 12/1995 | Yao .................... 606/98 |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,068,630 A | 5/2000 | Zucherman et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,447,513 B1 | 9/2002 | Griggs |
| 6,451,019 B1 | 9/2002 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,611,316 B2 | 11/2009 | Panasik et al. |
| 7,988,708 B2 * | 8/2011 | Yeh .................... 606/248 |
| 2002/0143331 A1 | 10/2002 | Zucherman et al. |
| 2003/0040746 A1 | 2/2003 | Mitchell et al. |
| 2003/0065330 A1 | 4/2003 | Zucherman et al. |
| 2003/0153915 A1 | 8/2003 | Nekozuka et al. |
| 2004/0097931 A1 | 5/2004 | Mitchell |
| 2004/0133204 A1 | 7/2004 | Davies |
| 2004/0167625 A1 | 8/2004 | Beyar et al. |
| 2004/0260397 A1 | 12/2004 | Lambrecht et al. |

(56) References Cited

U.S. PATENT DOCUMENTS

| | | |
|---|---|---|
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0293662 A1 | 12/2006 | Boyer, II et al. |
| 2006/0293663 A1 | 12/2006 | Walkenhorst et al. |
| 2007/0032790 A1 | 2/2007 | Aschmann et al. |
| 2007/0043362 A1 | 2/2007 | Malandain et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233081 A1 | 10/2007 | Pasquet et al. |
| 2007/0233089 A1 | 10/2007 | DiPoto et al. |
| 2007/0265625 A1* | 11/2007 | Zucherman et al. ............ 606/61 |
| 2007/0270834 A1 | 11/2007 | Bruneau et al. |
| 2007/0276369 A1 | 11/2007 | Allard et al. |
| 2007/0276493 A1 | 11/2007 | Malandain et al. |
| 2007/0282443 A1 | 12/2007 | Globerman et al. |
| 2008/0021457 A1 | 1/2008 | Anderson et al. |
| 2008/0058934 A1 | 3/2008 | Malandain et al. |
| 2008/0161818 A1 | 7/2008 | Kloss et al. |
| 2008/0183211 A1 | 7/2008 | Lamborne et al. |
| 2008/0183218 A1 | 7/2008 | Mueller et al. |
| 2008/0221685 A9 | 9/2008 | Altarac et al. |
| 2008/0262617 A1 | 10/2008 | Froehlich et al. |
| 2009/0234389 A1 | 9/2009 | Chuang et al. |
| 2009/0270918 A1 | 10/2009 | Attia et al. |
| 2010/0268277 A1* | 10/2010 | Bruneau et al. ............... 606/249 |

FOREIGN PATENT DOCUMENTS

| | | |
|---|---|---|
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

(56) References Cited

OTHER PUBLICATIONS

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopéclique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: indications, Technique, Results," Italian J. Spinal Disorders, 2003, pp. 213-220, vol. 3, No. 2.

Schlegel et al., "The Role of Distraction in improving the Space Available in the Lumbar Stenotic Canal and Foramen," SPINE, 1994, pp. 2041-2047, vol. 19, No. 18.

Senegas et al., "Le Recalibrage du Canal Lornbaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Rnvuc de Medécine Orthopédique, Jun. 1990, pp. 33-35, No. 20.

Senecas, "La Ligamentopiastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future." 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor at al., "Analyse d'une expérience clinique: d'un implant postérieur amortissant," Rachis Revue de Pathologie Vertébrale, Oct./Nov. 1999, vol. 11, No. 4-5, Gieda Inter Rachis.

Taylor at al. "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

(56) References Cited

OTHER PUBLICATIONS

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

\* cited by examiner

INTERSPINOUS PROCESS IMPLANT AND METHOD OF IMPLANTATION

BACKGROUND

This invention relates generally to the treatment of spinal conditions, and more particularly, to the treatment of spinal stenosis using devices for implantation between adjacent spinous processes.

The clinical syndrome of neurogenic intermittent claudication due to lumbar spinal stenosis is a frequent source of pain in the lower back and extremities, leading to impaired walking, and causing other forms of disability in the elderly. Although the incidence and prevalence of symptomatic lumbar spinal stenosis have not been established, this condition is the most frequent indication of spinal surgery in patients older than 65 years of age.

Lumbar spinal stenosis is a condition of the spine characterized by a narrowing of the lumbar spinal canal. With spinal stenosis, the spinal canal narrows and pinches the spinal cord and nerves, causing pain in the back and legs. It is estimated that approximately 5 in 10,000 people develop lumbar spinal stenosis each year. For patients who seek the aid of a physician for back pain, approximately 12%-15% are diagnosed as having lumbar spinal stenosis.

Common treatments for lumbar spinal stenosis include physical therapy (including changes in posture), medication, and occasionally surgery. Changes in posture and physical therapy may be effective in flexing the spine to decompress and enlarge the space available to the spinal cord and nerves—thus relieving pressure on pinched nerves. Medications such as NSAIDS and other anti-inflammatory medications are often used to alleviate pain, although they are not typically effective at addressing spinal compression, which is the cause of the pain.

Surgical treatments are more aggressive than medication or physical therapy, and in appropriate cases surgery may be the best way to achieve lessening of the symptoms of lumbar spinal stenosis. The principal goal of surgery is to decompress the central spinal canal and the neural foramina, creating more space and eliminating pressure on the spinal nerve roots. The most common surgery for treatment of lumbar spinal stenosis is direct decompression via a laminectomy and partial facetectomy. In this procedure, the patient is given a general anesthesia as an incision is made in the patient to access the spine. The lamina of one or more vertebrae is removed to create more space for the nerves. The intervertebral disc may also be removed, and the adjacent vertebrae may be fused to strengthen the unstable segments. The success rate of decompressive laminectomy has been reported to be in excess of 65%. A significant reduction of the symptoms of lumbar spinal stenosis is also achieved in many of these cases.

Alternatively, the vertebrae can be distracted and an interspinous process device implanted between adjacent spinous processes of the vertebrae to maintain the desired separation between the vertebral segments. Such interspinous process devices typically work for their intended purposes, but some could be improved. For example, many currently available interspinous process devices are challenging to properly place between adjacent spinous processes because of the space limitations in that area, which is filled with various muscles, ligaments, bone and other tissue. Some devices require a posterior to anterior approach. These types of devices are undesirable because they require that both the interspinous ligament and the supraspinous ligament be cut, or otherwise manipulated to allow the physician to gain access to the space between adjacent interspinous processes. In any surgical procedure, it is desirable to minimize trauma to surrounding tissue as much as possible in order to minimize recovery time for the patient and to provide the patient with the greatest chance for a successful outcome.

In view of the challenges with interspinous process devices that require a posterior to anterior approach, some devices have been designed that allow for a lateral approach. Some of these devices are significant improvements over those devices that require a direct posterior to anterior approach. However, even some devices that allow for a lateral approach to the space between adjacent spinous processes have challenges. As noted above, the space between adjacent spinous processes is confined. Thus it is difficult for the surgeon to manipulate the device to ensure that it is properly located in the space and to ensure that the device remains properly positioned therein. Where additional manipulation of the device is necessary to ensure that the device remains properly positioned in the desired space, the spatial limitations would be a factor militating against ease of insertion.

Thus, a need exists for improvements in interspinous process devices.

SUMMARY OF THE INVENTION

The interspinous process device of this invention includes (i) a main body portion having a shaft that is adapted to be disposed between adjacent spinous processes and a distal retention member adapted to be disposed along a lateral side of a superior spinous process, and an inferior spinous process, and (ii) a proximal retention member adapted to be disposed along an opposite lateral side of the superior spinous process and the inferior spinous process. A damper ring may also be located around the shaft of the main body portion between the proximal and distal retention members for engagement with the superior and inferior spinous processes. The proximal retention member has a central portion that defines a central lumen into which a proximal portion of the shaft of the main body portion may be located. The proximal portion of the shaft and the central lumen are configured so that the proximal retention member is rotatable with respect to the main body portion. Preferably, the length of the major axis of the distal retention member is greater than the distance between adjacent spinous processes when they are distracted to the desired spacing. Preferably, the length of the minor axis of the distal retention member is about equal to the distance between the adjacent spinous processes when they are distracted to the desired spacing.

When the interspinous process device of this invention is in an implantation configuration, the proximal retention member is oriented such that its major axis extends in a direction that is substantially normal to the orientation of the major axis of the distal retention member. When the interspinous process device is in its locked and final configuration, the major axis of the proximal retention member extends in a direction that is substantially aligned with and parallel to the major axis of the distal retention member. The proximal portion of the shaft includes a portion of a locking mechanism that cooperates with a complementary portion formed within the central lumen of the proximal retention member. This locking mechanism ensures that when the major axes of the proximal retention member and the distal retention member extend in a direction that is aligned and parallel to each other, the proximal retention member is locked with respect to the main body portion. Thus, the device can remain fixed in place between adjacent spinous processes such that the shaft and damper ring are disposed between the adjacent spinous processes and are substantially perpendicular to, and cross through, the sagittal plane. In this position, the distal retention member is located along the distal side of the superior and inferior spinous processes and the proximal retention member is located along the proximal side of the superior and inferior spinous processes such that the major axes of the distal and proximal retention members extend in a direction that is generally parallel to the sagittal and coronal planes and generally normal to the axial plane.

With the interspinous process device of this invention in the implantation configuration described above, the distal retention member is inserted through the interspinous ligament, which has been dissected to create an opening therethrough. This allows passage of the distal retention member therethrough, and through the space between adjacent spinous processes with a lateral approach. The distal retention member is oriented such that the major axis of the distal retention member is generally parallel to the axial plane but oriented at an angle to the sagittal and coronal planes. In this orientation, the minor axis is generally parallel to the sagittal plane and coronal plane and generally normal to the axial plane. This ensures that the dimension of the distal retention member along its minor axis does not hinder movement of the interspinous process device of this invention into the space between adjacent spinous processes. The distal retention member thus may be passed through the space between adjacent spinous processes with minimal disruption to the surrounding tissue. Importantly, the supraspinous ligament remains undisturbed during the procedure. It may be necessary for a leading edge of the distal retention member to be first passed through the space between the adjacent interspinous processes, in order to properly position the device. Of course, the orientation of the distal retention member may have to be adjusted in order to be properly placed in position. For example, the distal retention member may have to be rotated around the (i) longitudinal axis of the device, (ii) its major axis, and/or (iii) its minor axis during some part, or all, of the implantation procedure.

Once the distal retention member is adjacent to the distal side of the adjacent spinous processes, the distal retention member may be rotated with respect to the proximal retention member. This locks the distal retention member with respect to the proximal retention member such that the major axis of the proximal retention member and the major axis of the distal retention member extend in a direction that is generally parallel to each other and the sagittal and coronal planes and is generally normal to the axial plane. As noted above, the major axes of the distal retention member and the proximal retention member define a dimension that is greater than the distance between adjacent spinous processes. Preferably the dimension of the proximal retention member along its major axis is greater than the dimension of the distal retention member along its major axis. Of course, the distance between the proximal retention member and the distal retention member should be slightly greater than the distance between the distal side of the adjacent spinous process and the proximal side of the adjacent spinous processes. In this manner, the interspinous process device of this invention is held in place by the proximal and distal retention members and the shaft and/or the damper ring prevents the space between the adjacent spinous processes from collapsing during extension of the spine.

DETAILED DESCRIPTION

Figure 1:
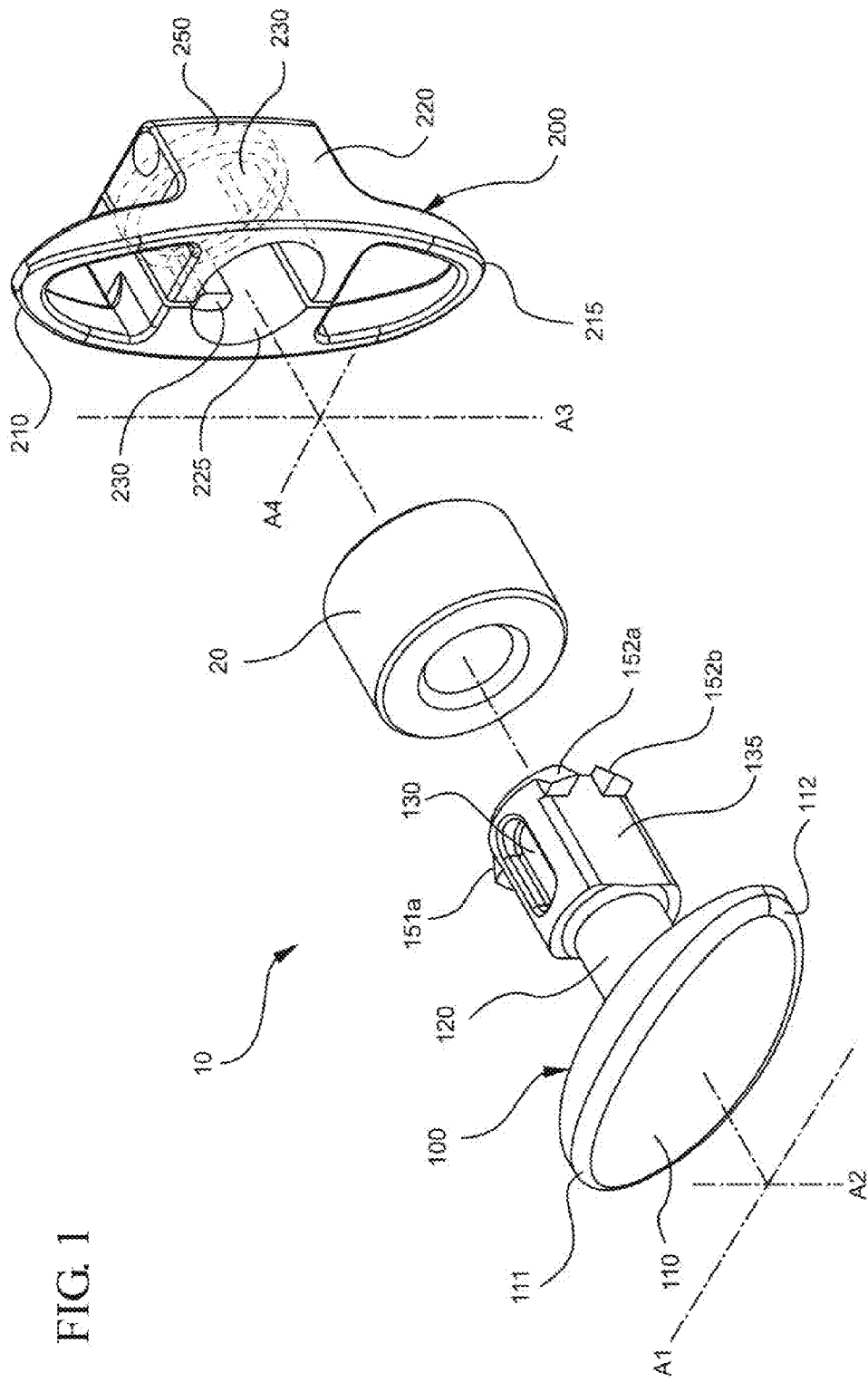
FIG. 1 is an exploded perspective view of the interspinous process device of this invention viewed from the distal end of the device.
Figure 2:
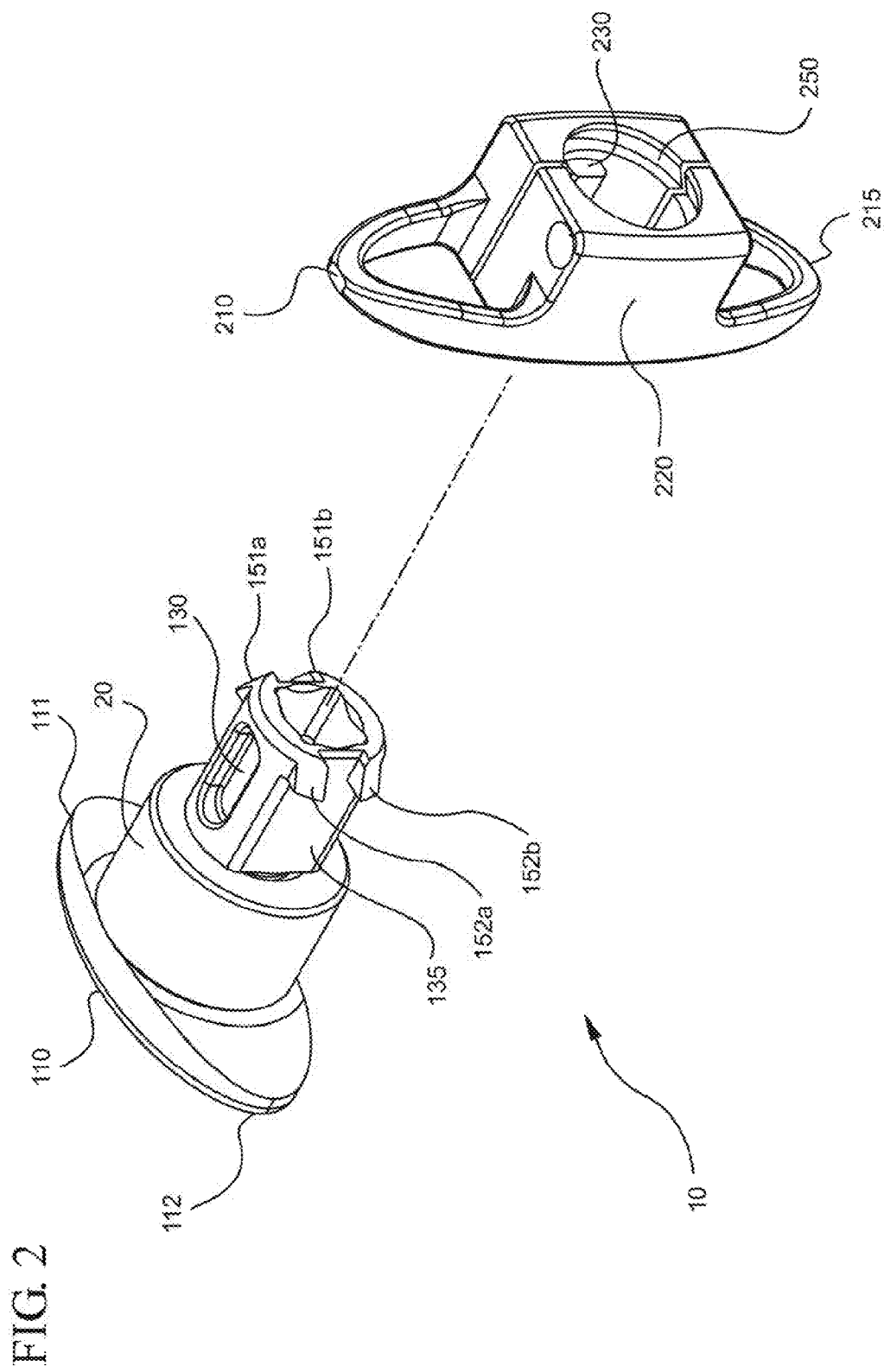
FIG. 2 is a partially exploded perspective view of the interspinous process device of this invention viewed from the proximal end of the device.

As used in this specification and the appended claims, the singular forms "a," "an" and "the" include plural referents unless the context clearly dictates otherwise. Thus, for example, the term "a member" is intended to mean a single member or a combination of members, and "a material" is intended to mean one or more materials, or a combination thereof. Furthermore, the words "proximal" and "distal" refer to directions closer to and away from, respectively, an operator (e.g., surgeon, physician, nurse, technician, etc.) who would insert the medical device into the patient, with the tip-end (i.e., distal end) of the device inserted inside a patient's body first. Thus, for example, the device end first inserted inside the patient's body would be the distal end of the device, while the device end last to enter the patient's body would be the proximal end of the device.

As used in this specification and the appended claims, the term "body" when used in connection with the location where the device of this invention is to be placed to treat lumbar spinal stenosis, or to teach or practice implantation methods for the device, means a mammalian body. For example, a body can be a patient's body, or a cadaver, or a portion of a patient's body or a portion of a cadaver.

As used in this specification and the appended claims, the term "parallel" describes a relationship, given normal manufacturing or measurement or similar tolerances, between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

As used in this specification and the appended claims, the terms "normal", "perpendicular" and "orthogonal" describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal, perpendicular or orthoganal to a curved surface when the line and the curved surface intersect at an angle of approximately 90 degrees within a plane. Two geometric constructions are described herein as being "normal", "perpendicular", "orthogonal" or "substantially normal", "substantially perpendicular", "substantially orthogonal" to each other when they are nominally 90 degrees to each other, such as for example, when they are 90 degrees to each other within a tolerance. Such tolerances can include, for example, manufacturing tolerances, measurement tolerances or the like.

The interspinous process device 10 of this invention includes (i) a main body portion 100 having a shaft 120 that is adapted to be disposed between adjacent spinous processes and a distal retention member 110 adapted to be disposed along a lateral side of a superior spinous process and an inferior spinous process, and (ii) a proximal retention member 200 adapted to be disposed along an opposite lateral side of the superior spinous process and the inferior spinous process. A damper ring 20 may also be located around shaft 120 of main body portion 100 between distal retention member 110 and proximal retention member 200. Preferably the proximal portion of shaft 120 has a larger diameter than the remainder of shaft 120 to define a recessed area between distal retention member 110 and the proximal portion of shaft 120 into which damper ring 20 may fit. See e.g. FIG. 1. Proximal retention member 200 includes a central portion 220 which defines a central lumen 225 into which a proximal portion of shaft 120 of main body portion 100 may be located so that proximal retention member 200 is rotatable with respect to main body portion 100.

Figure 15:
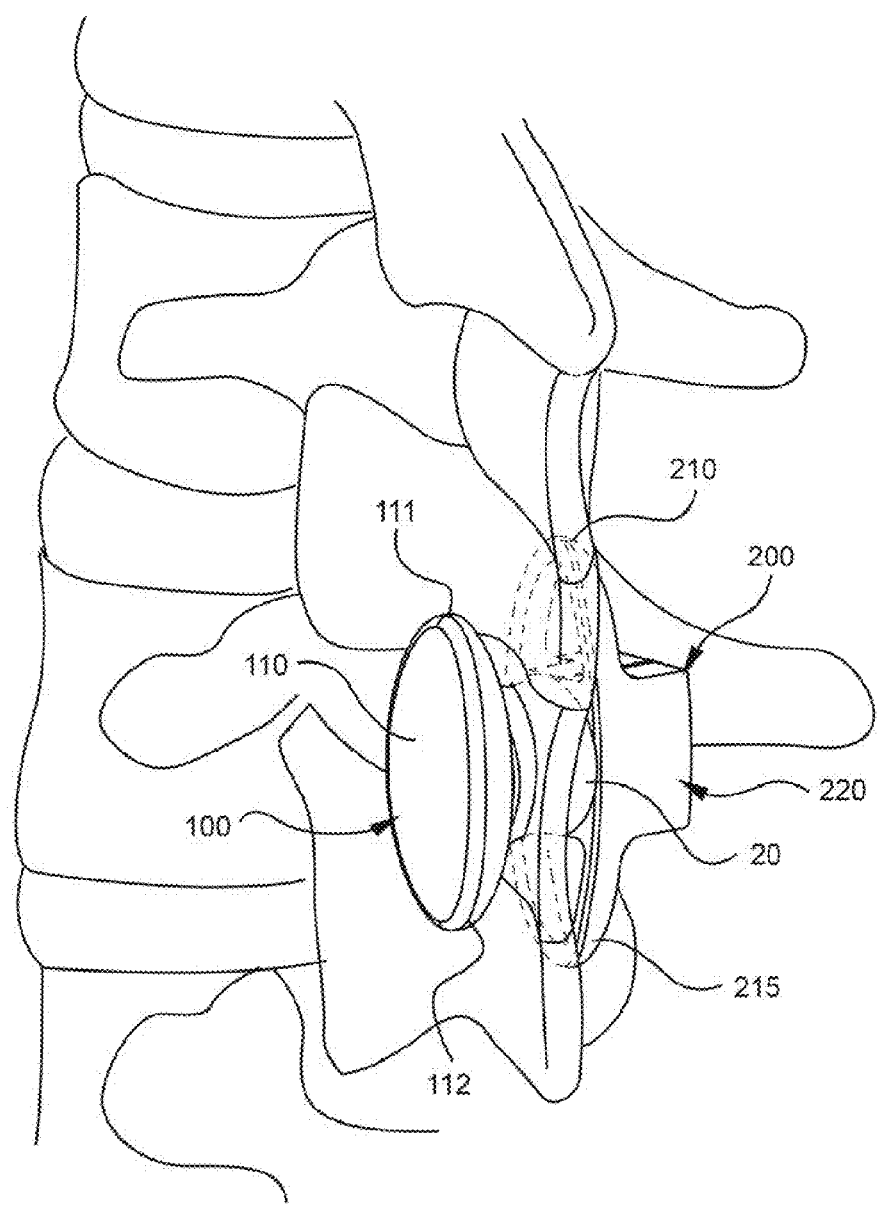

Distal retention member 110 includes a distal upper wing 111 and a distal lower wing 112. Distal upper wing 111 is adapted to engage a distal side of a superior spinous process when device 10 is appropriately located in the space between adjacent spinous processes such that the longitudinal axis of damper ring 20 is generally perpendicular to the sagittal plane. See for example FIG. 15. In this position, distal lower wing 112 is adapted to engage a distal side of an inferior spinous process. As shown herein, distal retention member 110 has a generally elliptical configuration with a major axis A1 and a minor axis A2. Although an elliptical configuration is preferred, any other geometrical shape may be used as long as distal retention member 110 presents a smaller dimension in a first direction than in a direction normal to the first direction. The dimension of distal retention member 110 along the major axis A1 is greater than the distance between adjacent spinous processes when they are distracted to the desired spacing. Preferably, the dimension of distal retention member 110 along the minor axis A2 is about equal to the distance between the adjacent spinous processes when they are distracted to the desired spacing.

The proximal portion of shaft 120 includes a slot 130 that cooperates with a complementary key 230 disposed within central lumen 225 of proximal retention member 200. Preferably two slots 130 are located along the proximal portion of shaft 120 about 180 degrees apart. Even more preferably, slots 130 are aligned 180 degrees apart so that they are aligned along a line extending in a direction substantially parallel to the minor axis A2 of distal retention member 110. A plurality of lugs is also spaced around the periphery of shaft 120 adjacent to its proximal end. Preferably, these lugs are divided into two sets of lugs, which are spaced about 180 degrees apart such that each set is located between the pair of slots 130. As shown, upper lugs 151a and 151b are generally aligned with distal upper wing 111, while lower lugs 152a and 152b are generally aligned with distal lower wing 112. In addition, generally planar surfaces 135 are located along the proximal portion of shaft 120 about 180 degrees apart, with each of planar surfaces 135 located adjacent to one set of lugs between each of slots 130. Stated another way, planar surfaces 135 are substantially aligned along a line extending in a direction substantially parallel to major axis A1.

Proximal retention member 200 includes a proximal upper wing 210 and a proximal lower wing 215, as well as a central portion 220 and central lumen 225. As shown herein, proximal retention member 200 has a generally elliptical configuration with a major axis A3 and a minor axis A4. Proximal retention member 200 is formed as a circumferential bar. However, proximal retention member 200 may have a solid configuration similar to distal retention member 110. In addition, distal retention member 110 may be formed as a circumferential bar similar to proximal retention member 200. Although an elliptical configuration is preferred for the configuration of proximal retention member 200, any other geometrical shape may be used as long as proximal retention member 200 presents a smaller dimension in a first direction than in a direction normal to the first direction. The dimension of proximal retention member 200 along the major axis A3 is greater than the distance between adjacent spinous processes when they are distracted to the desired spacing. The length of proximal retention member 200 along major axis A3 is preferably greater than the length of distal retention member 110 along major axis A1. This greater dimension provides a visual cue for the surgeon so s/he can quickly determine which end is the proximal portion and which end is the distal portion. In addition, it is preferable that distal retention member 110 be relatively small to facilitate implantation of the device. Typically, there is less room on the distal side of the spinous processes for the surgeon to manipulate the device.

A key 230 is formed in central lumen 225 in complementary receiving fashion with respect to slot 130. Preferably two such keys 230 are formed in central lumen 225 and are located about 180 degrees apart along the minor axis A4. This allows keys 230 to be aligned with planar surfaces 135 when the major axis A1 of distal retention member 110 extends in a direction that is normal to the major axis A3 of proximal retention member 200.

An annular groove 250 is formed along an internal surface of central lumen 225 along a proximal portion thereof. Annular groove 250 is formed to act as a guide for lugs 151a, 151b, 152a, and 152b. As such, lugs 151a, 151b, 152a, and 152b fit within annular groove 250 and can move along groove 250 as proximal retention member 200 rotates with respect to main body portion 100 about the longitudinal axis of main body portion 100. Preferably, lugs 151a, 151b, 152a and 152b have tapered proximal ends to facilitate the movement of lugs 151a, 151b, 152a and 152b into annular groove 250 as main body portion 100 is moved in a direction along the longitudinal axis of shaft 120 into engagement with proximal retention member 200 during assembly of device 10. Preferably lugs 151a, 151b, 152a and 152b have a distal end that is substantially perpendicular to planar surface 135. This ensures that lugs 151a, 151b, 152a and 152b are difficult to remove from annular groove 250 and minimizes the possibility that main body portion 100 can be removed from proximal retention member 200 once device 10 is assembled. In addition, lugs 151a and 151b are separated a distance that is at least slightly greater than the width of key 230. Similarly, lugs 152a and 152b are separated a distance that is at least slightly greater than the width of key 230. This allows keys 230 to move past lugs 151a, 151b, 152a and 152b during assembly such that keys 230 are adjacent planar surfaces 135. Planar surfaces 135 provide sufficient space between the wall of central lumen 225 to allow keys 230 and the proximal portion of shaft 120 to fit within central lumen 225.

Key 230 and slot 130 are configured such that key 230 fits snugly within slot 130. Thus, when main body portion 100 is rotated with respect to proximal retention member 200 so that major axis A1 of distal retention member 110 extends in a direction that is aligned with and parallel to the major axis A3 of proximal retention member 200, key 230 drops into slot 130 to lock proximal retention member 200 with respect to main body portion 100. This ensures that when device 10 is in its locked configuration, device 10 can be located between adjacent spinous processes with shaft 120 and damper ring 20 located between adjacent spinous process such that they are substantially perpendicular to and cross the sagittal plane, distal upper wing 111 and distal lower wing 112 are located along the distal portion of the superior and inferior spinous processes respectively, and proximal upper retention member 210 and proximal lower retention member 215 are located along the proximal portion of the superior and inferior spinous processes respectively. This prevents device 10 from migrating from that location after implantation. Although a key and slot locking mechanism is preferred, other locking mechanisms may be used in connection with device 10 as long as the locking mechanism (i) allows relative rotation between main body portion 100 and proximal retention member 200, and (ii) locks main body portion 100 and proximal retention member 200 with respect to each other such that the major axis A1 of distal retention member 110 extends in the same direction as the major axis A3 of proximal retention member 200.

Figure 3:
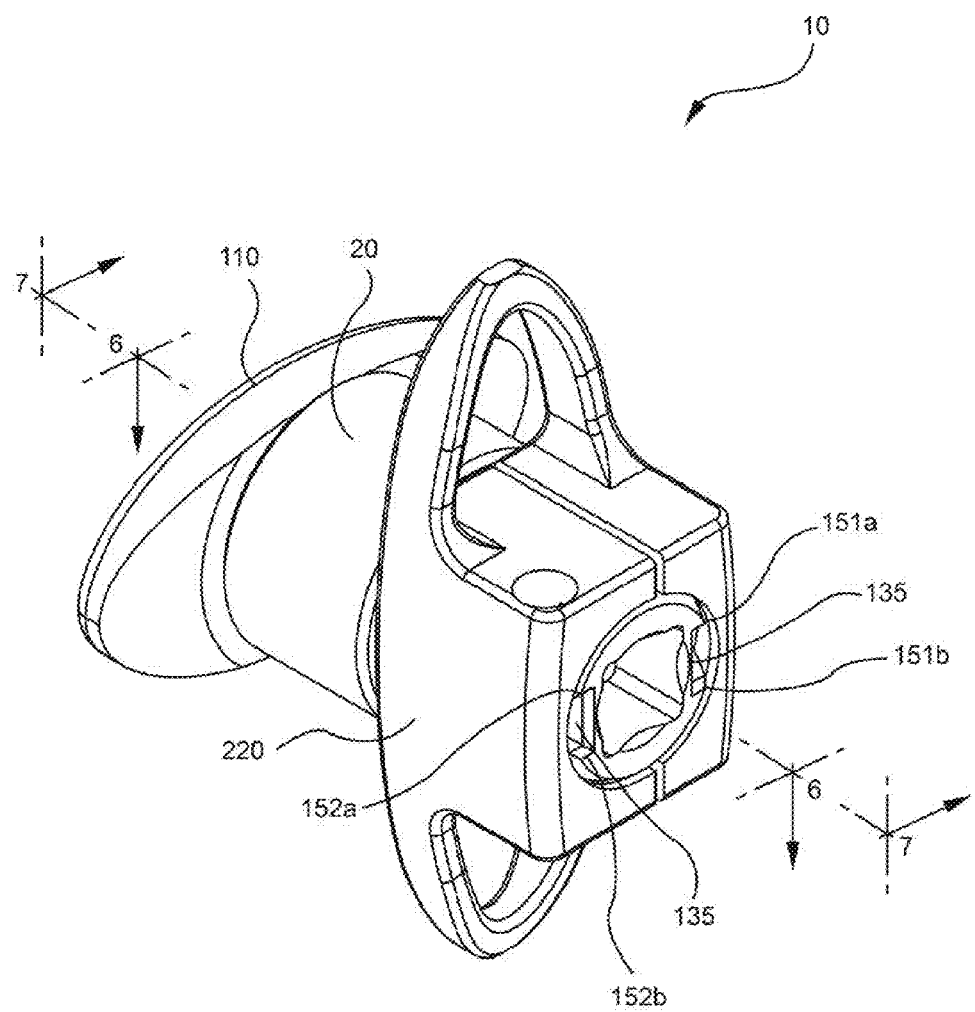
FIG. 3 is a proximal perspective view of the interspinous process device of this invention in the implantation configuration.
Figure 4:
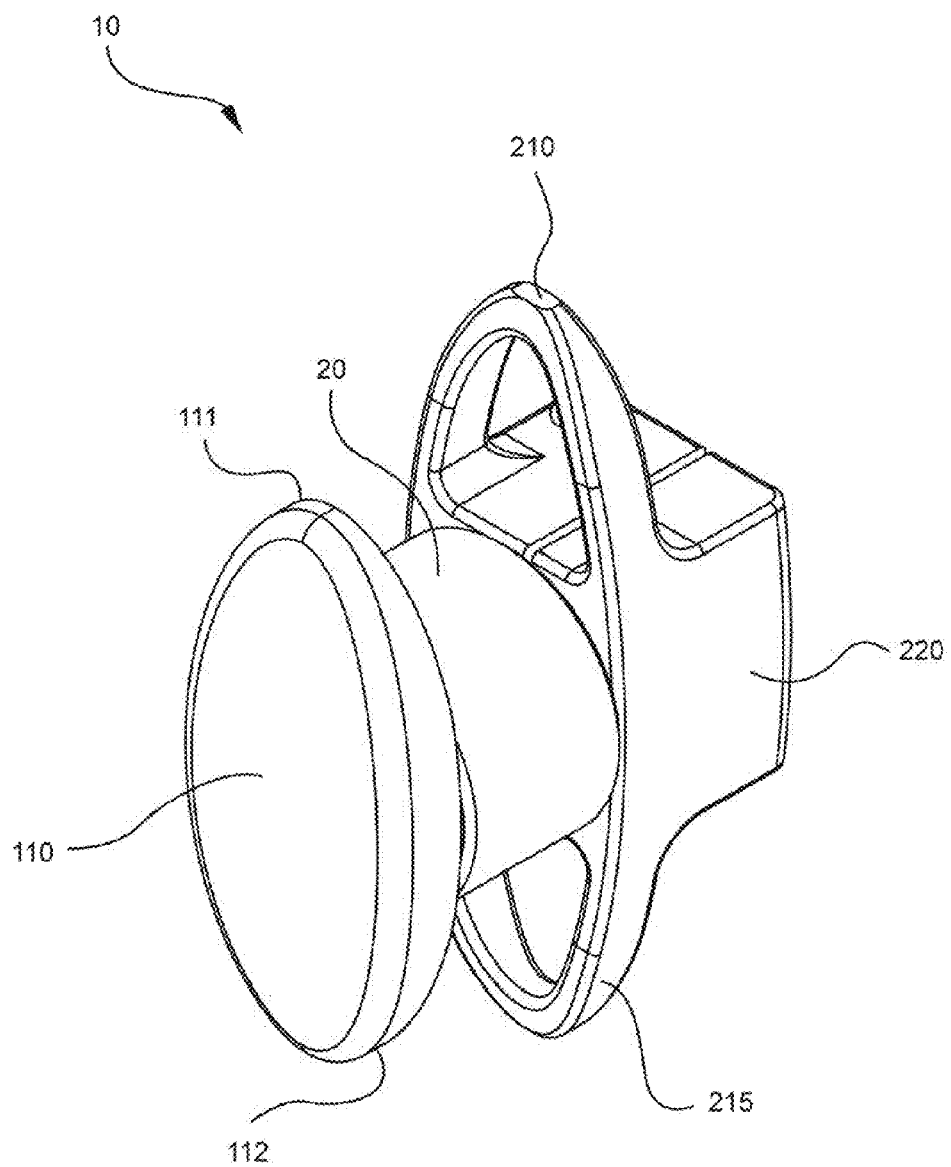
FIG. 4 is a distal perspective view of the interspinous process device of this invention in the locked configuration.
Figure 5:
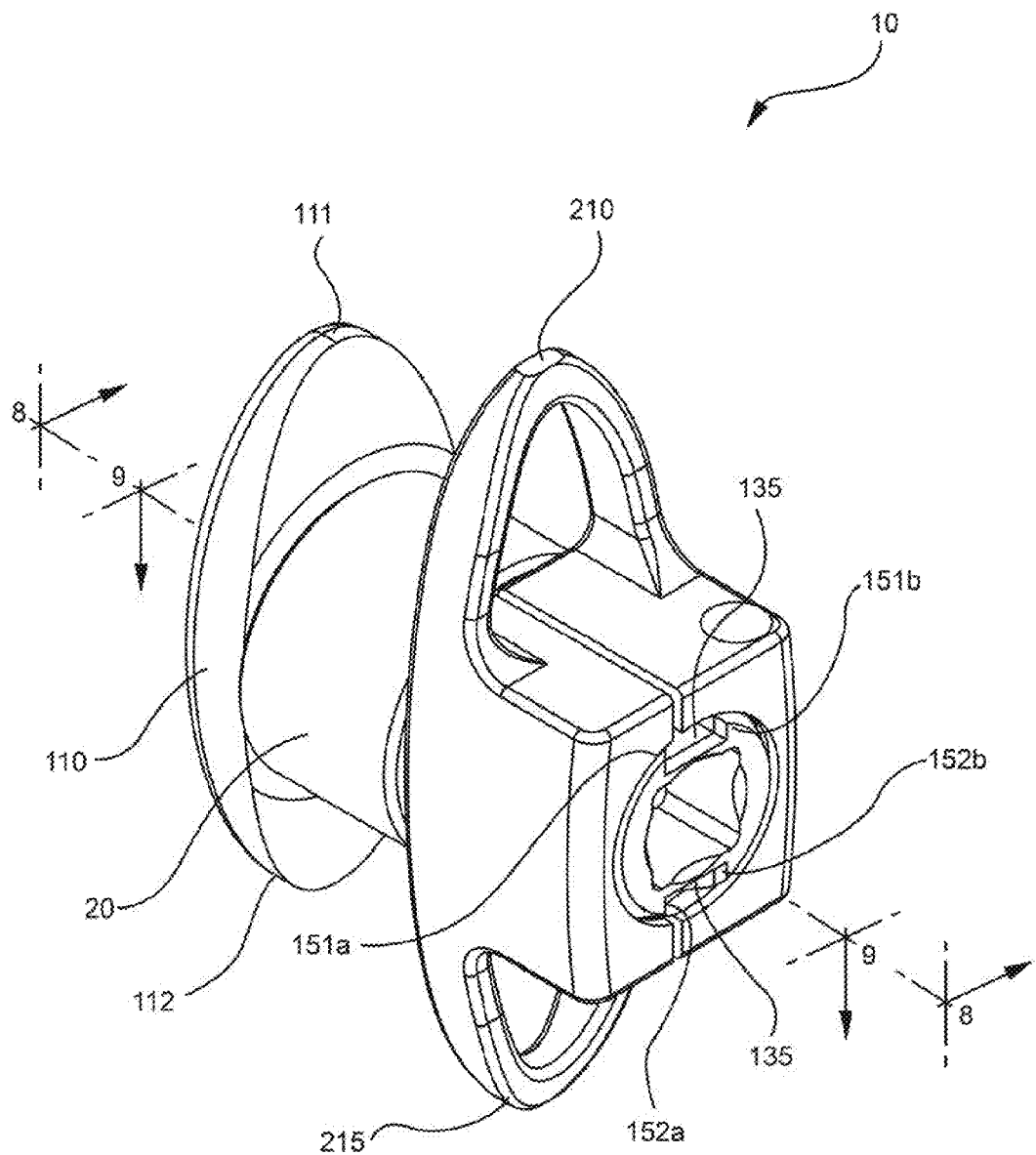
FIG. 5 is a proximal perspective view of the interspinous process device of this invention in the locked configuration.
Figure 6:
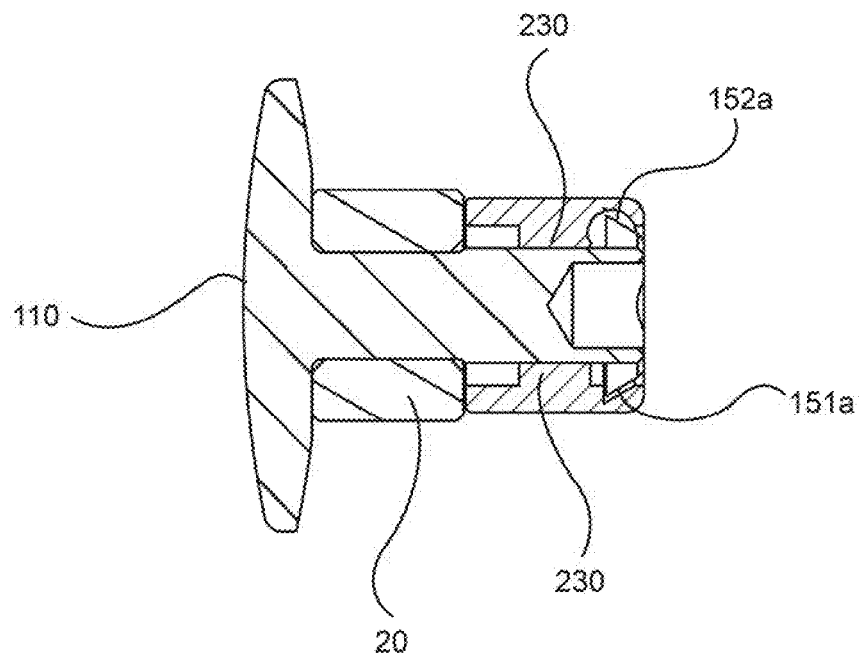
FIG. 6 is a cross-sectional view of the interspinous process device of this invention taken along lines 6-6 of FIG. 3.
Figure 7:
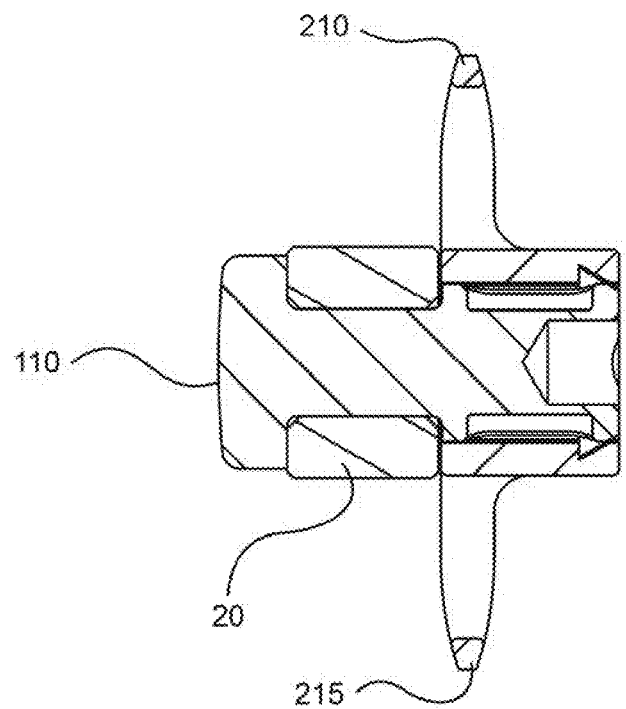
FIG. 7 is a cross-sectional view of the interspinous process device of this invention taken along lines 7-7 of FIG. 3.
Figure 8:
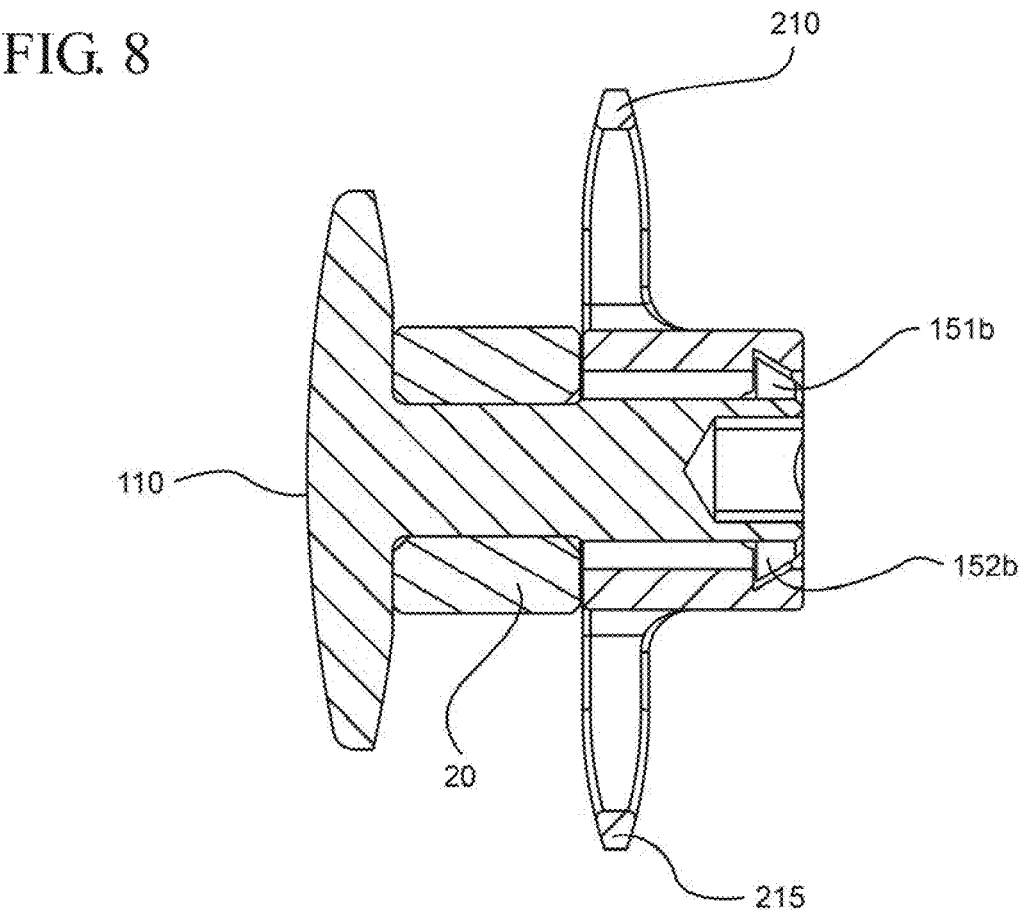
FIG. 8 is a cross-sectional view of the interspinous process device of this invention taken along lines 8-8 of FIG. 5.
Figure 9:
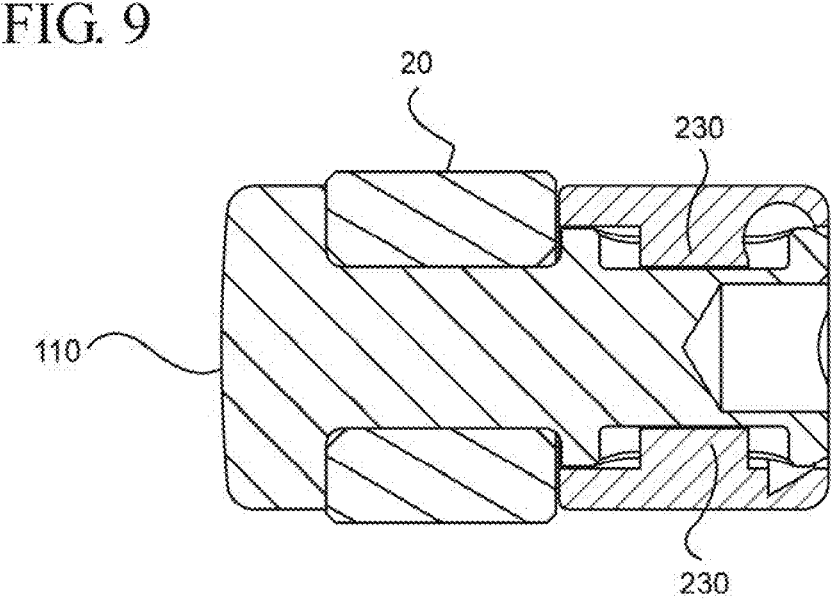
FIG. 9 is a cross-sectional view of the interspinous process device of this invention taken along lines 9-9 of FIG. 5.
Figure 10:
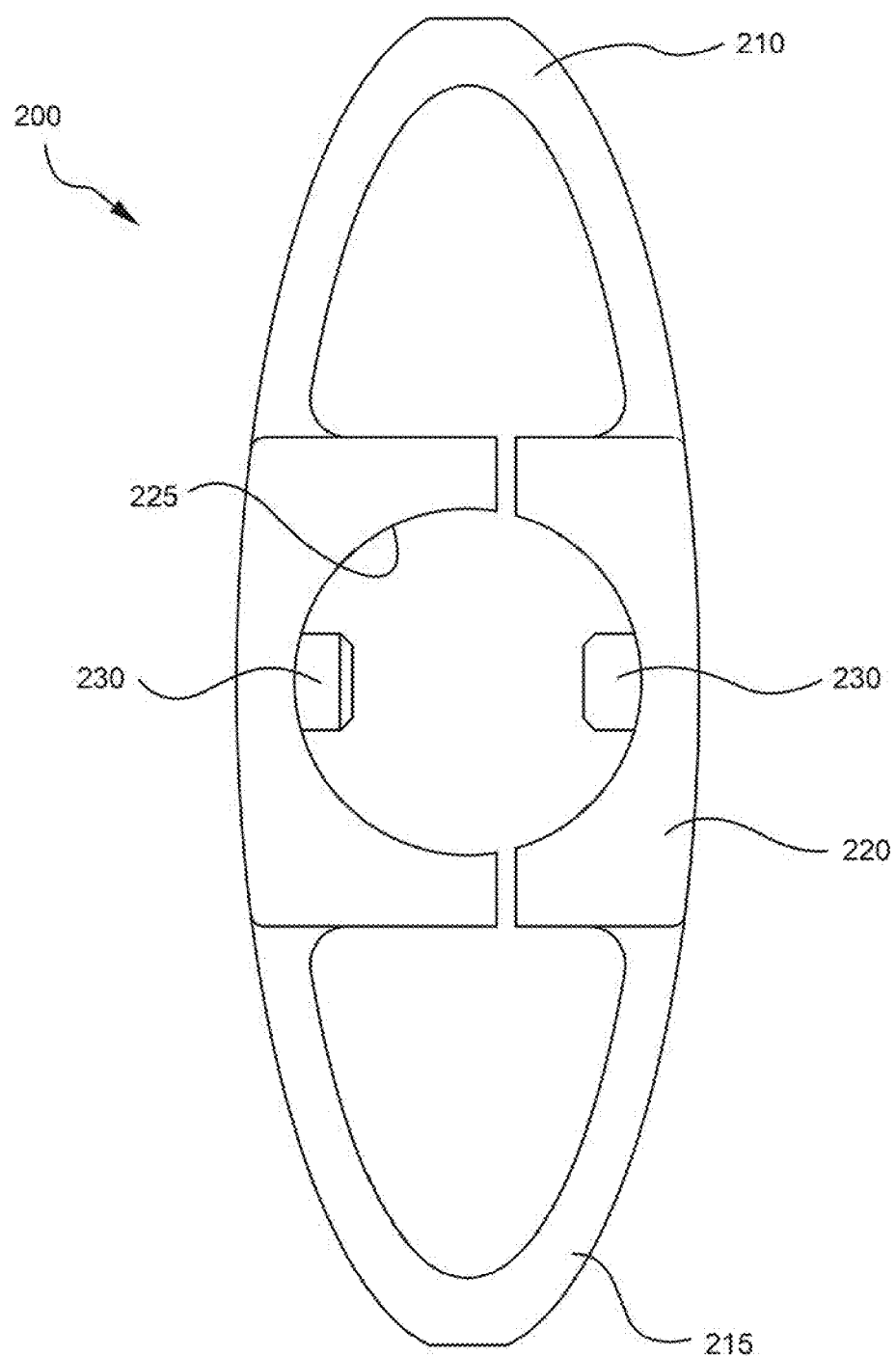
FIG. 10 is an end elevation view of the proximal retention member of the interspinous process device of this invention.

When device 10 is in the implantation configuration as shown for example in FIG. 3, proximal retention member 200 is oriented such that major axis A3 is substantially normal to the orientation of major axis A1 of distal retention member 110, i.e. major axis A3 extends in a direction substantially normal to the direction of major axis A1. When device 10 is in its locked and final configuration as shown for example in FIG. 5, major axis A3 of proximal retention member 200 extends in a direction that is substantially aligned with major axis A1 of distal retention member 110, i.e. major axis A3 extends in a direction substantially parallel to the direction of major axis A1. The arrangement of keys 230 and slots 130 allows main body portion 100 to be rotated with respect to proximal retention member 200 about 90 degrees in either a clockwise or counterclockwise direction between the initial implantation position and the final locked position.

Figure 11:
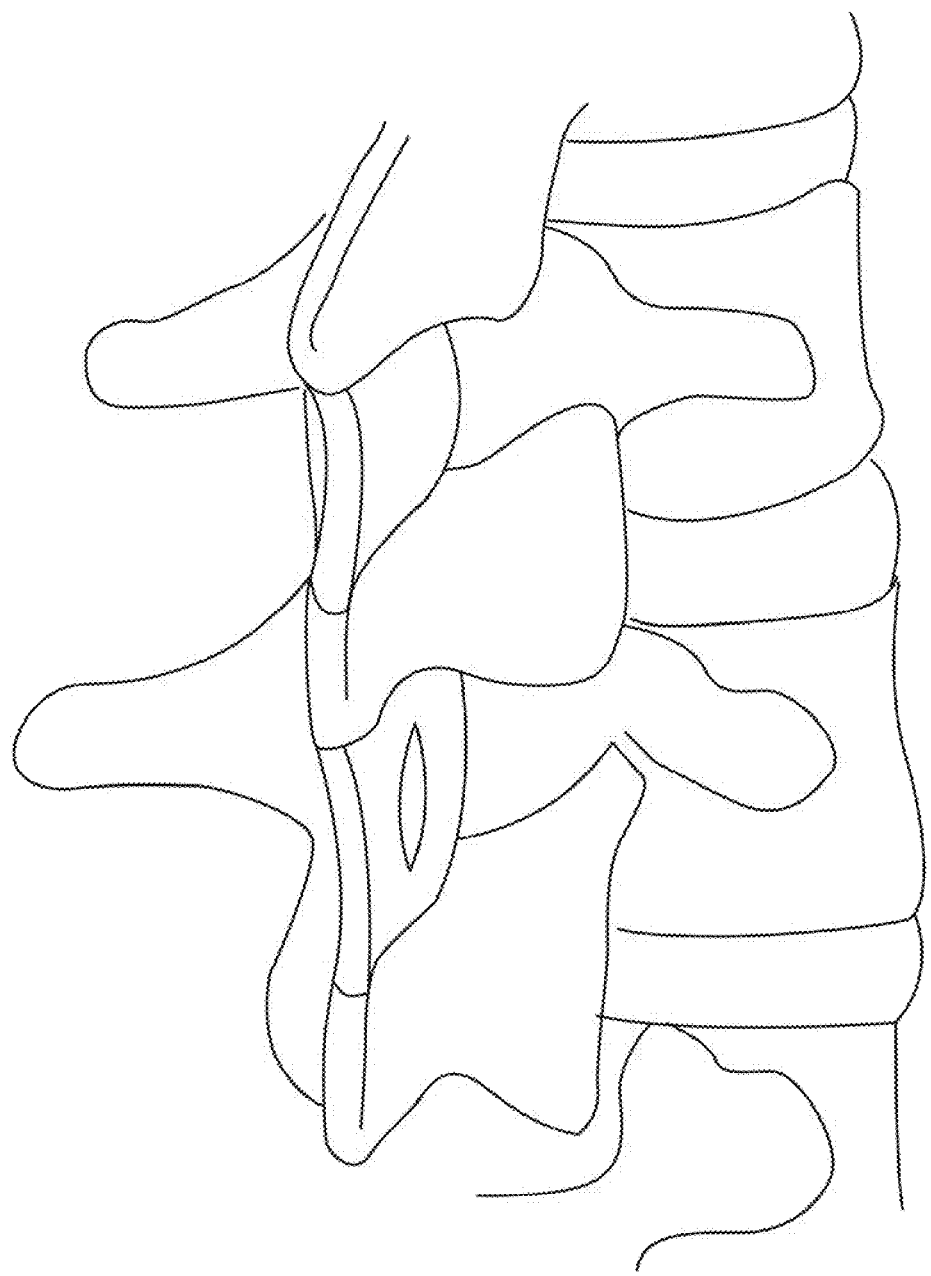
FIG. 11 is a schematic view of a portion of a human spine showing a dissected interspinous ligament in the space between adjacent spinous processes where the interspinous process device of this invention is to be implanted.

The interspinous ligament is typically dissected with a cutting instrument, such as a simple scalpel, an electrosurgical device or the like, not shown, to create an appropriately sized opening in the interspinous ligament to allow passage of a distal portion of device 10 therethrough. See FIG. 11. This allows device 10 to be implanted in the space between adjacent spinous processes with a lateral approach. In most circumstances, the space between adjacent spinous processes may first need to be distracted with a distraction tool, not shown, to provide additional space and pain relief for the patient. After the physician confirms sufficient distraction, device 10 can then be placed in the space between the adjacent spinous processes. Device 10 can come in different sizes to accommodate different amounts of distraction/space needed between adjacent spinous processes.

Figure 12:
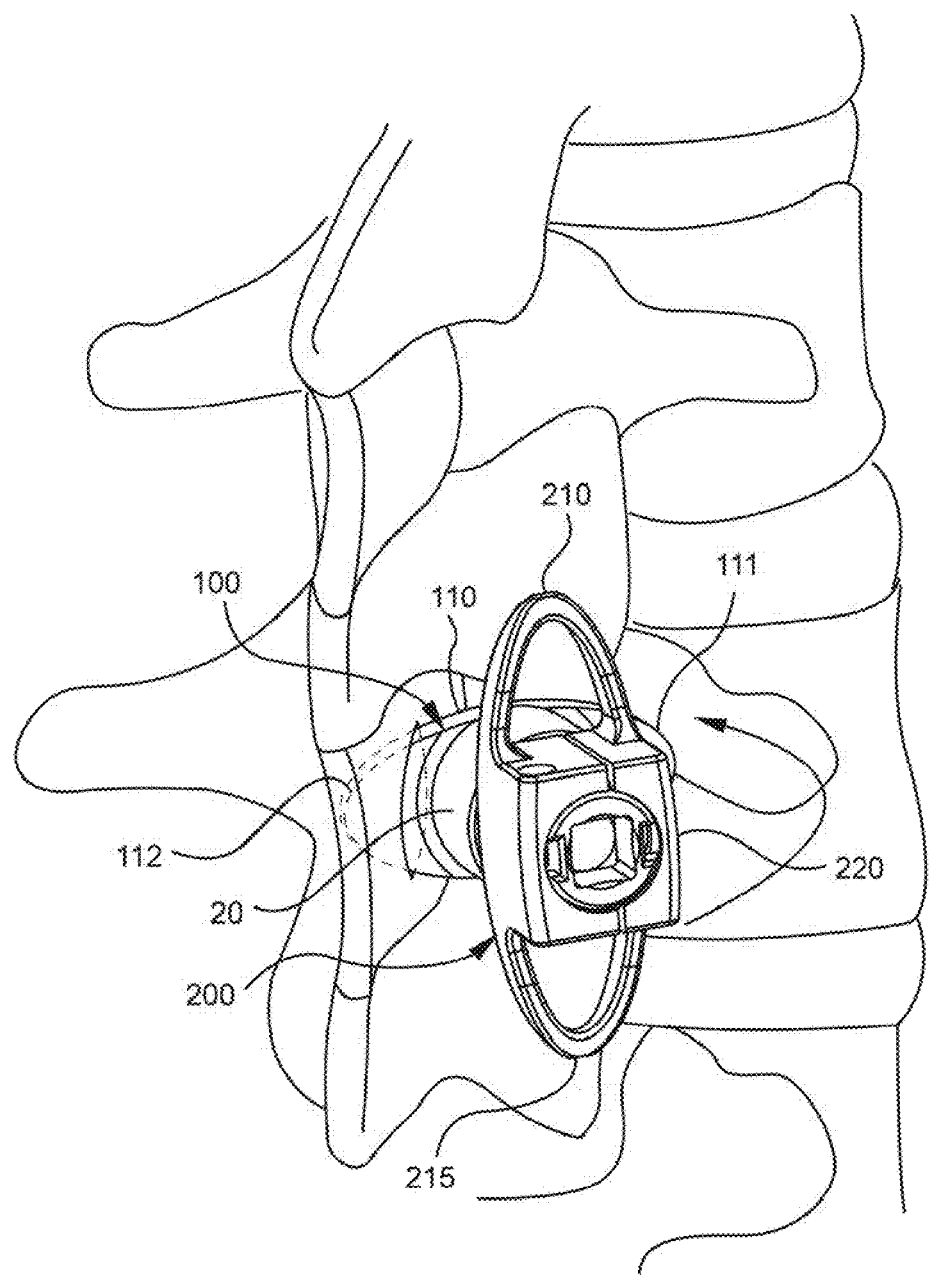
FIGS. 12-15 are schematic illustrations of the interspinous process device of this invention and a portion of a human spine that illustrate the method of implanting the interspinous process device of this invention.

With device 10 in the implantation configuration described above, distal retention member 110 is inserted through the opening formed in the interspinous ligament. See FIG. 12. Distal retention member 110 is oriented such that its major axis A1 is generally parallel to the axial plane, with minor axis A2 being generally parallel to the sagittal plane and the coronal plane. In this orientation, major axis A1 would not be parallel to or normal to the sagittal and coronal planes. See FIG. 12. In this orientation, the dimension of distal retention member 110 along minor axis A2 does not hinder movement of device 10 through the space between adjacent spinous processes. Distal retention member 110 thus may be passed through the space between adjacent spinous processes with minimal disruption to the surrounding tissue. Importantly, the supraspinous ligament remains undisturbed during the procedure. It may be necessary for a leading edge of distal retention member 110 to be first passed through the space between the adjacent interspinous processes, with major axis A1 not parallel to and not normal to the sagittal and coronal planes, in order to properly position device 10. Once the leading edge of distal retention member 110 passes through the space formed in the interspinous ligament, device 10 may be rotated about an axis normal to the longitudinal axis of implant 10 so the longitudinal axis of implant 10 becomes parallel to the coronal and axial planes and normal to the sagittal plane. Compare FIG. 12 with FIG. 13. This also places proximal retention member 200 along the proximal side of adjacent superior and inferior spinous processes with major axis A3 generally parallel to the sagittal and coronal planes and generally normal to the axial plane. Of course, the orientation of distal retention member 110 may have to be adjusted during the procedure in order to be properly placed in position. For example, distal retention member 110 may have to be rotated around the (i) longitudinal axis of device 10, (ii) its major axis, and/or (iii) its minor axis during some portion or all of the implantation procedure. These manipulations may be necessary because of individual characteristics of the anatomy of the body into which device 10 is to be located.

Figure 13:
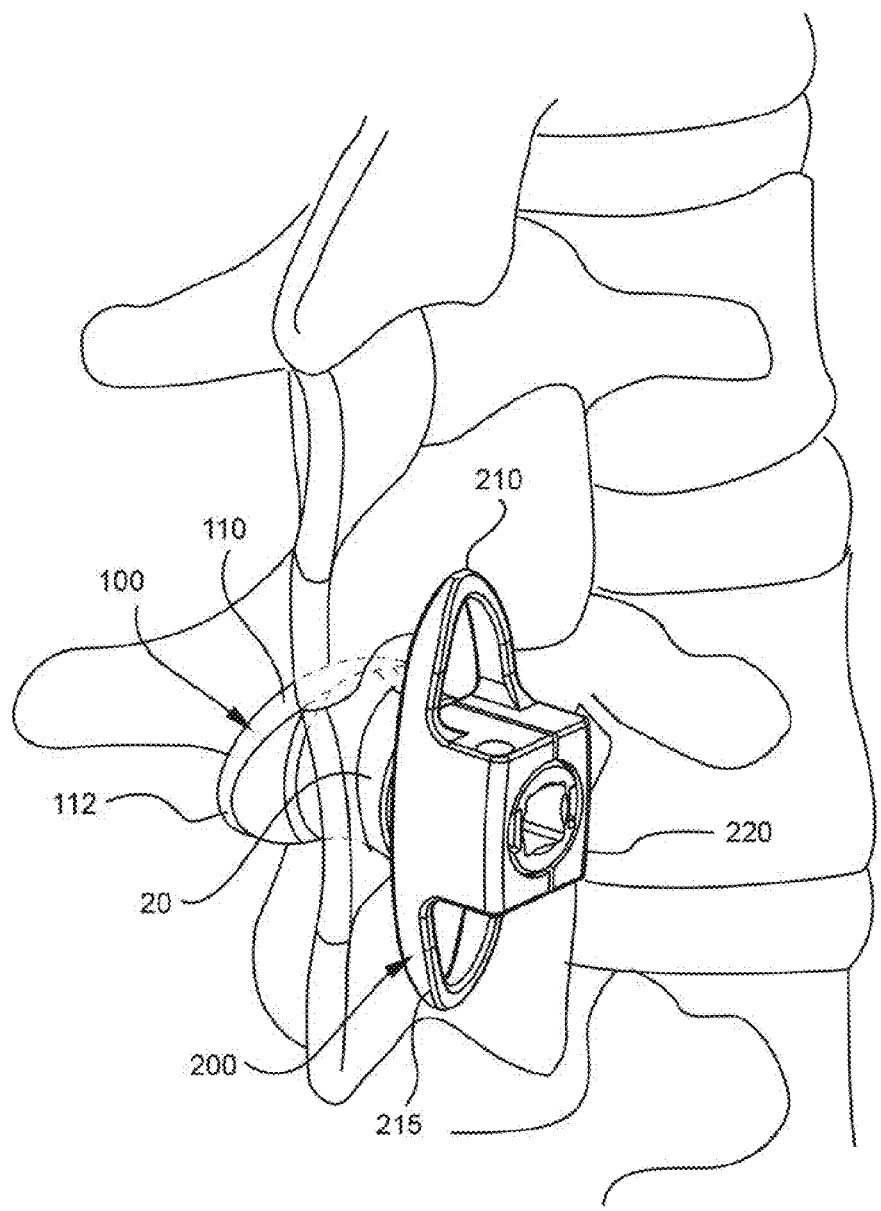
Figure 14:
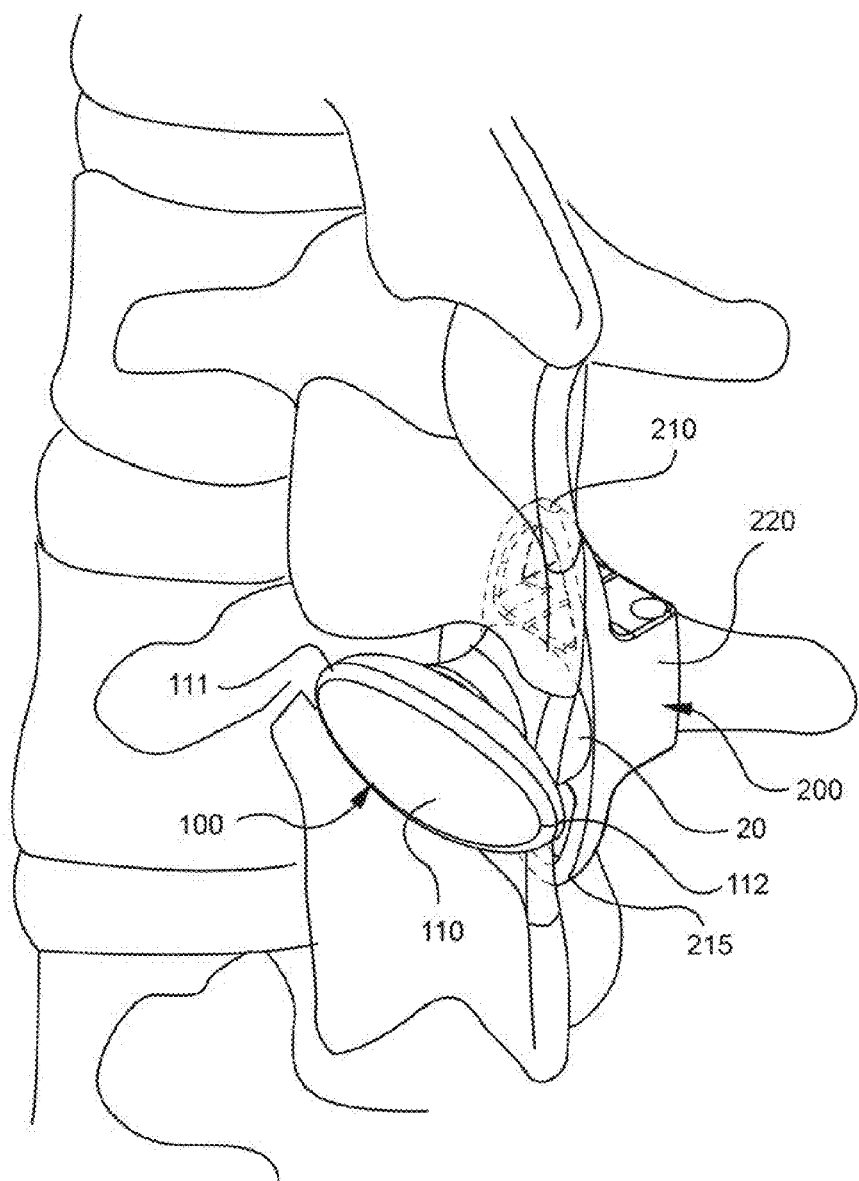

Once distal retention member 110 is adjacent to the distal side of the adjacent spinous processes, see FIGS. 13 and 14, distal retention member 110 may be rotated with respect to proximal retention member 200 about the longitudinal axis of main body portion 100. Distal retention member 110 may be rotated either clockwise or counterclockwise. This locks distal retention member 110 with respect to proximal retention member 200 such that major axis A3 of proximal retention member 200 and major axis A1 of distal retention member 110 are oriented such that they extend in the same direction and thus are generally parallel to each other and the sagittal and coronal planes and generally normal to the axial plane. As noted above, major axes A1 and A3 of distal retention member 110 and proximal retention member 200 respectively define a dimension that is greater than the distance between adjacent spinous processes, with the dimension for proximal retention member 200 preferably being greater. Of course, the distance between proximal retention member 200 and distal retention member 110 should be slightly greater than the distance between the distal side of the adjacent spinous process and the proximal side of the adjacent spinous processes.

In this manner, device 10 is held in place by proximal retention member 200 and distal retention member 110.

Device 10 can be constructed with various biocompatible materials such as, for example, titanium, titanium alloy, surgical steel, biocompatible metal alloys, stainless steel, Nitinol, plastic, polyetheretherketone (PEEK), carbon fiber, ultra-high molecular weight (UHMW) polyethylene, and other biocompatible polymeric materials. The material of device 10 can have, for example, a compressive strength similar to or higher than that of bone. In one embodiment, damper ring 20, which is placed between the two adjacent spinous processes, is formed from a material having an elastic modulus higher than the elastic modulus of the bone of the spinous processes. In another embodiment, damper ring 20 is formed from a material having a higher elastic modulus than the materials used to form main body portion 100 and proximal retention member 200. For example, damper ring 20 may have an elastic modulus higher than bone, while main body portion 100 and proximal retention member 100 have a lower elastic modulus than bone. Preferably, damper ring 20 is formed of a compliant material, such as silicone, to dampen the shock when the spinal column is moved into extension.

While various embodiments of the invention have been described above, it should be understood that they have been presented by way of example only, and not limitation. The foregoing description of the interspinous process device is not intended to be exhaustive or to limit the invention of the device. Many modifications and variations will be apparent to the practitioner skilled in the art. It is intended that the scope of the invention be defined by the following claims and their equivalents.

What is claimed is:

1. A device, comprising:
a first retention member having a central portion defining a longitudinal axis and an upper wing extending outward from the central portion transverse to the longitudinal axis, a lower wing extending outward from the central portion in a direction opposite to the upper wing and transverse to the longitudinal axis wherein the upper wing of the first retention member and the lower wing of the first retention member are configured to be disposed along a first side of a superior spinous process and an inferior spinous process; and
a main body portion extending along the longitudinal axis and having a second retention member including an upper wing extending outward from the main body portion transverse to the longitudinal axis a lower wing extending outward from the main body portion in a direction opposite to the upper wing and transverse to the longitudinal axis wherein the upper wing of the second retention member and the lower wing of the second retention member are configured to be disposed along a second side of a superior spinous process and an inferior spinous process opposite the first side and being rotatable with respect to the first retention member between a first position such that upper and lower wings of the main body are disposed perpendicular to the upper and lower wings of the first retention member and a second position such that upper and lower wings of the main body are disposed parallel to the upper and lower wings of the first retention member,
wherein the main body portion is rotatable between the first position and the second position.

2. The device of claim 1 wherein the longitudinal axis of the main body portion extends from a proximal portion to a distal portion of the main body portion and wherein the second retention member is adjacent to the distal portion.

3. The device of claim 2 wherein in the second position the main body portion is not rotatable with respect to the first retention member.

4. The device of claim 1 wherein the second retention member has a surface area that is smaller than the surface area of the first retention member.

5. The device of claim 1 further comprising a damper ring disposed about the main body portion between the first retention member and the second retention member.

6. The device of claim 1 wherein the first retention member defines a first major axis and a first minor axis and the second retention member defines a second major axis and a second minor axis such that in the first position the first major axis and the first minor axis extend in directions that are generally perpendicular to the directions in which the second major axis and the second minor axis respectively extend.

7. The device of claim 1 wherein the first retention member defines a first major axis and a first minor axis and the second retention member defines a second major axis and a second minor axis such that in the second position the first major axis and the first minor axis extend in directions that are generally parallel to the directions in which the second major axis and the second minor axis respectively extend.

8. The device of claim 7 further comprising a lock adapted to lock the first retention member and the main body portion in the second position.

9. A device, comprising:
a proximal retention member defining a central lumen therein, the proximal retention member includes a central portion defining a longitudinal axis and an upper wing extending outward from the central portion transverse to the longitudinal axis a lower wing extending outward from the central portion in a direction opposite to the upper wing and transverse to the longitudinal axis wherein the upper wing of the proximal retention member and the lower wing of the proximal retention member are configured to be disposed along a first side of a superior spinous process and an inferior spinous process;
a main body portion extending along the longitudinal axis and having a distal retention member and a shaft having a proximal portion and a distal portion extending proximally from the distal retention member wherein the proximal portion is disposed in the central lumen, the distal retention member including an upper wing extending outward from the main body portion transverse to the longitudinal axis a lower wing extending outward from the main body portion in a direction opposite to the upper wing and transverse to the longitudinal axis wherein the upper wing of the distal retention member and the lower wing of the distal retention member are configured to be disposed along a second side of a superior spinous process and an inferior spinous process opposite the first side;
at least one key disposed in the central lumen; and
the proximal portion of the shaft defining at least one slot adapted to engage the at least one key,
wherein the main body portion is rotatable between a first position such that upper and lower wings of the main body are disposed perpendicular to the upper and lower wings of the first retention member and a second position such that upper and lower wings of the main body are disposed parallel to the upper and lower wings of the first retention member.

10. The device of claim 9 wherein the proximal retention member includes a major axis and a minor axis and further comprising two keys located about 180 degrees apart along the minor axis.

11. The device of claim 10 wherein the distal retention member includes a major axis and a minor axis and the proximal portion of the shaft defines two slots therein about 180 degrees apart generally aligned along a line substantially parallel to the minor axis of the distal retention member.

12. The device of claim 10 wherein the proximal portion of the shaft defines two generally planar surfaces each disposed between the two slots.

13. The device of claim 12 further comprising a plurality of lugs disposed adjacent to the proximal portion of the shaft wherein the lugs are adjacent to the generally planar surfaces.

14. The device of claim 9 further comprising a plurality of lugs disposed adjacent to the proximal portion of the shaft.

15. The device of claim 14 further comprising an annular groove disposed about the central lumen adjacent to a proximal portion thereof with the plurality of lugs adapted to be disposed in and movable with respect to the annular groove.

16. The device of claim 9 further comprising a damper ring disposed about the shaft.

\* \* \* \* \*